United States Patent
Pallone

(10) Patent No.: US 10,342,692 B2
(45) Date of Patent: Jul. 9, 2019

(54) SPINE SUPPORT DEVICE FOR MAINTAINING ANATOMICAL ALIGNMENT AND STABILITY

(71) Applicant: Kevin Pallone, Parkland, FL (US)

(72) Inventor: Kevin Pallone, Parkland, FL (US)

(*) Notice: Subject to any disclaimer, the term of this patent is extended or adjusted under 35 U.S.C. 154(b) by 583 days.

(21) Appl. No.: 15/133,361

(22) Filed: Apr. 20, 2016

(65) Prior Publication Data

US 2017/0304105 A1 Oct. 26, 2017

(51) Int. Cl.
| | | |
|---|---|---|
| A61F 5/02 | (2006.01) | |
| A61F 7/00 | (2006.01) | |
| A61F 7/08 | (2006.01) | |
| A61F 7/10 | (2006.01) | |
| A61F 5/058 | (2006.01) | |

(52) U.S. Cl.
CPC .............. *A61F 5/028* (2013.01); *A61F 5/024* (2013.01); *A61F 5/05883* (2013.01); *A61F 7/08* (2013.01); *A61F 7/10* (2013.01); *A61F 2007/0024* (2013.01)

(58) Field of Classification Search
CPC ........ A61F 5/028; A61F 7/10; A61F 5/05883; A61F 5/024; A61F 7/08; A61F 2007/0024
USPC .......................................................... 602/19
See application file for complete search history.

(56) References Cited

U.S. PATENT DOCUMENTS

| | | | |
|---|---|---|---|
| 3,068,860 A | 12/1962 | Strazdas | |
| 5,107,826 A | 4/1992 | Andersson | |
| 5,179,944 A | 1/1993 | McSymytz | |
| 5,228,458 A * | 7/1993 | Ciacca | A61F 5/028 128/845 |
| 5,433,689 A * | 7/1995 | Frins | A63B 21/00047 128/845 |
| 6,074,413 A | 6/2000 | Davis et al. | |
| 7,195,605 B1 | 3/2007 | White | |
| 7,198,609 B2 | 4/2007 | Rolnick et al. | |
| 7,247,145 B2 * | 7/2007 | Kancilja | A44B 11/006 602/19 |
| 8,742,196 B2 | 6/2014 | Arbesman et al. | |
| 2008/0319365 A1 | 12/2008 | Kendrick | |

* cited by examiner

*Primary Examiner* — Tarla R Patel
(74) *Attorney, Agent, or Firm* — Glenn E. Gold, P.A.; Glenn Gold

(57) ABSTRACT

A spine support device includes a support plate having front and rear faces, a central opening, and a pair of stabilizing stirrups formed on the rear face of the support plate in spaced parallel relationship to augment the support provided by the support plate when positioned at its front face in contact with a portion of a person's back surrounding a region of spinal vertebra visible through the central opening in the support plate. The support plate has opposing inner side edge portions at opposing sides of the central opening and opposite peripheral side edge portions spaced outwardly therefrom with the stabilizing stirrups therebetween. The opposing inner side edge portions and the opposite peripheral side edge portions of the support plate have respective alternating peak and valley shapes for accommodating interconnecting facets of the spinal vertebra region visible through the central opening in the support plate.

15 Claims, 14 Drawing Sheets

SPINE SUPPORT DEVICE FOR MAINTAINING ANATOMICAL ALIGNMENT AND STABILITY

FIELD OF THE INVENTION

The present invention relates generally to human spine support devices, and, more particularly, is concerned with such spine support devices intended for use by individuals to correct anatomically improper spinal alignment, for maintaining anatomically proper spinal alignment and normal spinal curvature, and for imparting spinal stability for relief of lower back pain and neck pain.

BACKGROUND OF THE INVENTION

Low back pain is one of the most common health issues people face. In the United States alone, approximately 60% to 80% of the adult population suffer from low back pain and/or neck pain. Back pain is the leading cause of disability in Americans under 45 years of age. It is the second most common reason people cite for seeking medical attention. Every year, approximately 13 million people seek medical treatment for chronic back pain. The condition leaves about 2.4 million Americans chronically disabled, and another 2.4 million temporarily disabled. Approximately $90 billion is spent on the diagnosis and management of low back pain, with an additional $10-20 billion of annual economic losses attributed to the corresponding reduction in worker productivity.

In most cases, low back and neck pain are the direct result of poor anatomical spinal alignment. Individuals living with poor spinal alignment may suffer from restricted spinal flexibility, spinal instability, and reduced strength. These conditions often lead to chronic pain, discomfort and stiffness, which correspondingly reduce, and otherwise negatively impact, the affected individual's quality of life while going about normal, everyday functional activities, recreational activities, work-related activities, sports-related activities, and the like.

Most back pain can be prevented by maintaining proper spinal alignment and making sure to practice good body mechanics, such as maintaining proper posture while lifting heavy objects, participating in everyday recreational activities, or playing in sporting events in a way that won't strain the back.

Elastic therapeutic tape, commonly referred to as "kinesiology tape," is a widely used approach for addressing muscle and joint pain and disability; particularly, among athletes. A major drawback, or shortcoming, commonly associated with taping is that it is too flimsy and oftentimes does not provide adequate structural support. It is used primarily as a feedback mechanism while attached to the skin in order to prevent the occurrence of an abnormal, or otherwise undesirable, posture. However, taping does not adequately restrict motion, nor prevent an individual from maintaining an abnormal, or undesirable, posture because the tape's inherently high degree of structural flexibility precludes its use for providing sufficient anatomical support and/or maintaining proper anatomical alignment. Other conventional approaches, which are inherently more structurally sound than tape, include the use of braces and adhesive foam supports. However, conventional braces and adhesive supports typically lack an accurate anatomical design, fail to incorporate means for conforming to the unique anatomical variations from person to person, restrict an individual user's optimal range of motion, and provide less-than-optimal support of the spine. Furthermore, donning conventional bracing presents a host of additional issues; for example, bracing is often cumbersome, difficult to apply, and, because it is normally worn over clothing, causes the individual wearer to become uncomfortably hot and sweaty. Likewise, adhesive foam supports are generally uncomfortable and restrict, or limit, proper anatomic range of motion. Furthermore, these and other known approaches are not designed to mimic, or conform to, the normal anatomy of the human spine. Consequently, currently-available products and associated methods do not allow for appropriate degrees of freedom of motion, or movement, of the spine in an anatomically correct manner, do not provide optimal desired spinal support, and do not provide means for correcting male alignment.

Accordingly, there remains a need in the art for an innovation that will overcome the aforementioned deficiencies and limitations of known devices, products and methods.

SUMMARY OF THE INVENTION

The present invention is directed to an innovation that overcomes the deficiencies of the known art and the problems that remain unsolved by providing a spine support device for maintaining and correcting anatomical alignment and stability for relief of back pain problems. The spine support device provides a physical/mechanical support to the spine which can be easily applied before, during or after an activity or a sporting event in order to maintain proper alignment of the spine, thus improving a person's natural support in order to prevent or reduce back pain. The unique design of the spine support device is such that it can enable self-adhesive attachment and also it conforms to the natural anatomy of the spine so as to allow for rotation of the spine and, at the same time, provide the stability and support the spine needs to function properly.

In one aspect of the present invention, a spine support device includes:
 a support plate having a substantially flat configuration, the support plate including
  front and rear faces, and
  a central opening between the front and rear faces thereof; and
 a pair of stabilizing stirrups formed on the rear face of the support plate in spaced-apart parallel relationship to one another to augment the support provided by the support plate when the support plate at its front face is positioned in contact with a portion of a person's back surrounding a region of spinal vertebra of the person visible through the central opening in the support plate that is intended to be supported by the support plate.

In another aspect of the present invention, the front face of the support plate may have an adhesive layer thereon for detachably attaching the support plate to the portion of the person's back surrounding the person's spinal vertebra section that is visible through the central opening in the support plate.

In another aspect of the present invention, each of the stabilizing stirrups protrudes outwardly from the rear face of the support plate and includes an elongated outer body defining an elongated cavity, and an elongated inner body disposed in the elongated cavity. Further, each of the outer and inner bodies and the elongated cavity has a length and a width and is greater in the length than the width. Further, the elongated outer body of each stabilizing stirrup may have a closed lower end and an open upper end through which the elongated inner body may be inserted into the elongated cavity of the elongated outer body and rest upon the closed lower end thereof. Alternatively, the elongated outer body of each stabilizing stirrup may have a strip covering the elongated cavity being peelable therefrom to open the elongated cavity and permit insertion of the elongated inner body in the form of one of a heated applicator, a cooled applicator and a medicated applicator into the opened elongated cavity.

In another aspect of the present invention, a spine support device includes:
- a support plate including
  - front and rear faces,
  - a central opening between the front and rear faces and having opposing sides, and
  - opposing inner side edge portions at the opposing sides of the central opening, each of the opposing inner side edge portions having an alternating peak and valley shape such that the opposing inner side edge portions are mirror images of one another for accommodating interconnecting facets of a region of spinal vertebra of a person visible through the central opening in the support plate when the support plate at its front face is positioned in contact with a portion of the person's back surrounding the spinal vertebra region that is intended to be supported by the support plate; and
- a pair of stabilizing stirrups formed on and protruding outwardly from the rear face of the support plate in spaced-apart parallel relationship to one another and spaced outwardly from the opposing inner side edge portions of the support plate so as to augment the support provided by the support plate when the support plate is positioned in contact with the portion of a person's back.

In another aspect of the present invention, a spine support device includes:
- a support plate including
  - front and rear faces,
  - a central opening between the front and rear faces,
  - opposite peripheral top and bottom edge portions spaced apart from one another, and
  - opposite peripheral side edge portions spaced apart from one another and extending longitudinally between and interconnecting the opposite peripheral top and bottom edge portions, each of the opposite peripheral side edge portions having an alternating peak and valley shape such that the opposite peripheral side edge portions are mirror images of one another for accommodating interconnecting facets of a region of spinal vertebra of a person visible through the central opening in the support plate when the support plate at its front face is positioned in contact with a portion of the person's back surrounding the spinal vertebra region that is intended to be supported by the support plate; and
- a pair of stabilizing stirrups formed on and protruding outwardly from the rear face of the support plate in spaced-apart parallel relationship to one another and spaced inwardly from the opposite peripheral side edge portions of the support plate so as to augment the support provided by the support plate when the support plate is positioned in contact with the portion of the person's back.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Figure 1:
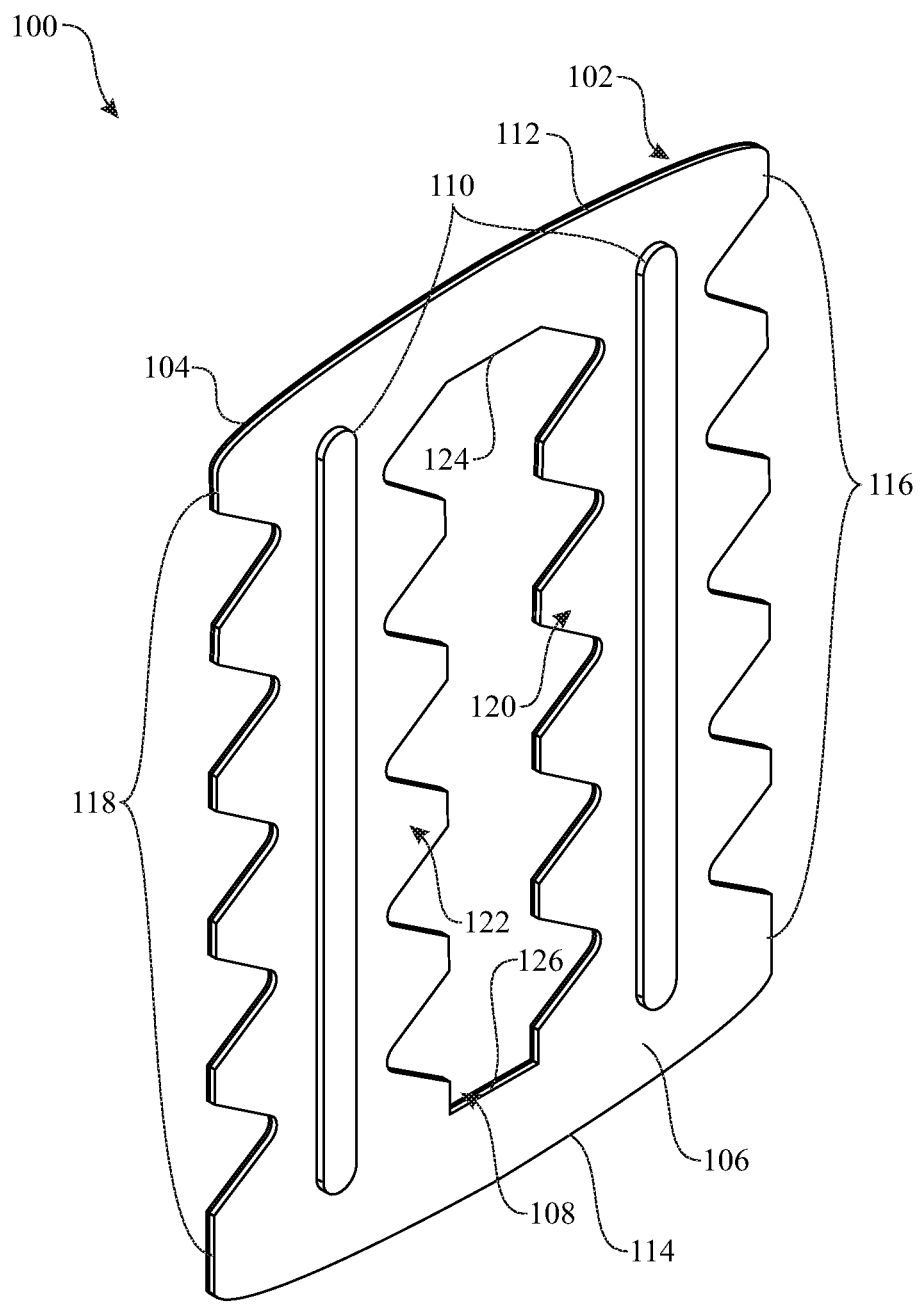
FIG. 1 presents a rear isometric view of a first exemplary embodiment of a spine support device, in accordance with aspects of the present invention, having a pair of stabilizing stirrups of a first design.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-4, there is illustrated a first exemplary embodiment of a spine support device, generally designated 100, which, in accordance with aspects of the present invention, enables the maintenance and correction of anatomical alignment and stability for relief of back pain problems. The spine support device 100 provides a physical/mechanical support of a selected region of the spinal vertebra of a person which can be easily applied on the person's back adjacent to the selected region of the spinal vertebra before, during or after an activity or a sporting event in order to assist in maintaining and or correcting proper alignment of the spinal vertebra, thus improving the person's natural support in order to prevent or reduce back pain. The configuration of the spine support device 100 is such that it can enable self-adhesive attachment to the person's back. Also, the configuration of the spine support device 100 conforms to the natural anatomy of the spine so as to allow for rotation of the spine and, at the same time, provide the stability and support the spine needs to function properly.

More particularly, the spine support device 100 includes a support plate 102 having a substantially flat, or planar, configuration with front and rear faces 104, 106, a central opening 108 defined through the support plate 102 between its front and rear faces 104, 106, and a pair of stabilizing stirrups 110 on the support plate 102 being substantially identical to one another. The stabilizing stirrups 110 are formed on and protruding outwardly from the rear face 106 of the support plate 102. The stabilizing stirrups 110 are designed to augment the effectiveness of the support provided by the spine support device 100 when the support plate 102 at its front face 104 is positioned in contact with a portion of a person's back surrounding the selected spinal vertebra region of the person visible through the central opening 108 in the support plate 102 that is intended to be supported by the spine support device 100.

The support plate 102 also has opposite peripheral top and bottom edge portions 112, 114 spaced apart from one another and opposite peripheral side edge portions 116, 118 spaced apart from one another and extending longitudinally between and interconnecting the opposite peripheral top and bottom edge portions 112, 114. Each of the opposite peripheral side edge portions 116, 118 has an alternating peak and valley shape such that the opposite peripheral side edge portions are mirror images of one another for accommodating interconnecting facets of the selected spinal vertebra region of the person that is intended to be supported by the support plate 102. The opposite peripheral top and bottom edge portions 112, 114 have oppositely curved shapes being mirror images of one another. The curved design or shape allows for a more anatomical fit below the thoracic spinal region and also at the base of the pelvis. The alternating peak and valley shape defines a plurality, such as five in number, of notches that especially match the lumbar spinal region for allowing rotation of the person's spine.

Further, the support plate 102 also includes opposing inner side edge portions 120, 122 at opposing sides of the central opening 108. Each of the opposing inner side edge portions 120, 122 has an alternating peak and valley shape such that the opposing inner side edge portions are mirror images of one another also for accommodating the interconnecting facets of the selected spinal vertebra region of the person that is intended to be supported by the support plate 102. The support plate 102 also has opposing inner upper and lower edge portions 124, 126 at opposing top and bottom ends of the central opening 108. The opposing inner upper and lower edge portions 124, 126 are in a spaced-apart parallel relationship to one another.

Figure 4:
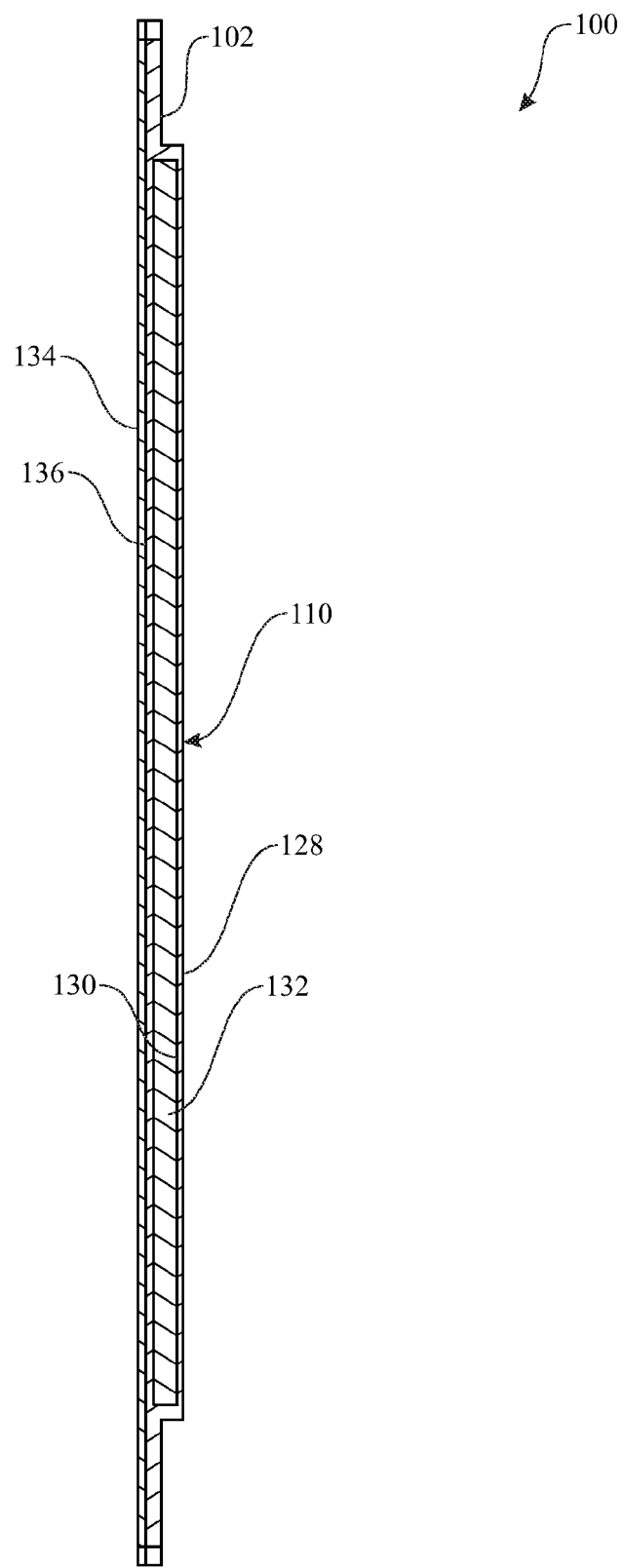
FIG. 4 presents an enlarged longitudinal cross-sectional view of the spine support device 100 taken along section line 4-4 of FIG. 3.
Figure 5:
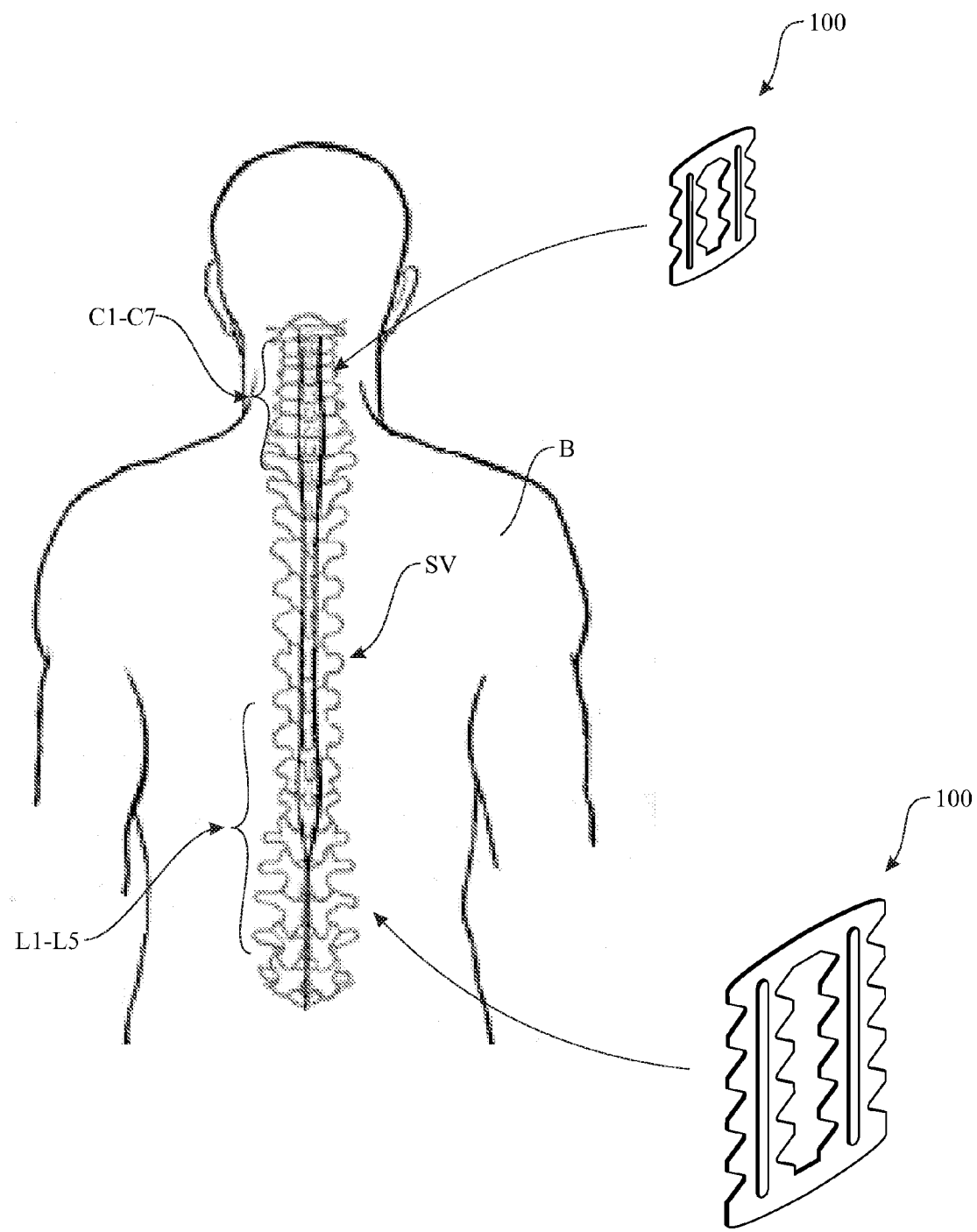
FIG. 5 presents a rear pictorial view of a human spine depicted in a person's body with arrows and corresponding reference characters identifying particular cervical and lumbar regions of the spine prior to application of corresponding appropriately-sized spine support devices, such as the exemplary device 100 introduced in FIG. 3.
Figure 6:
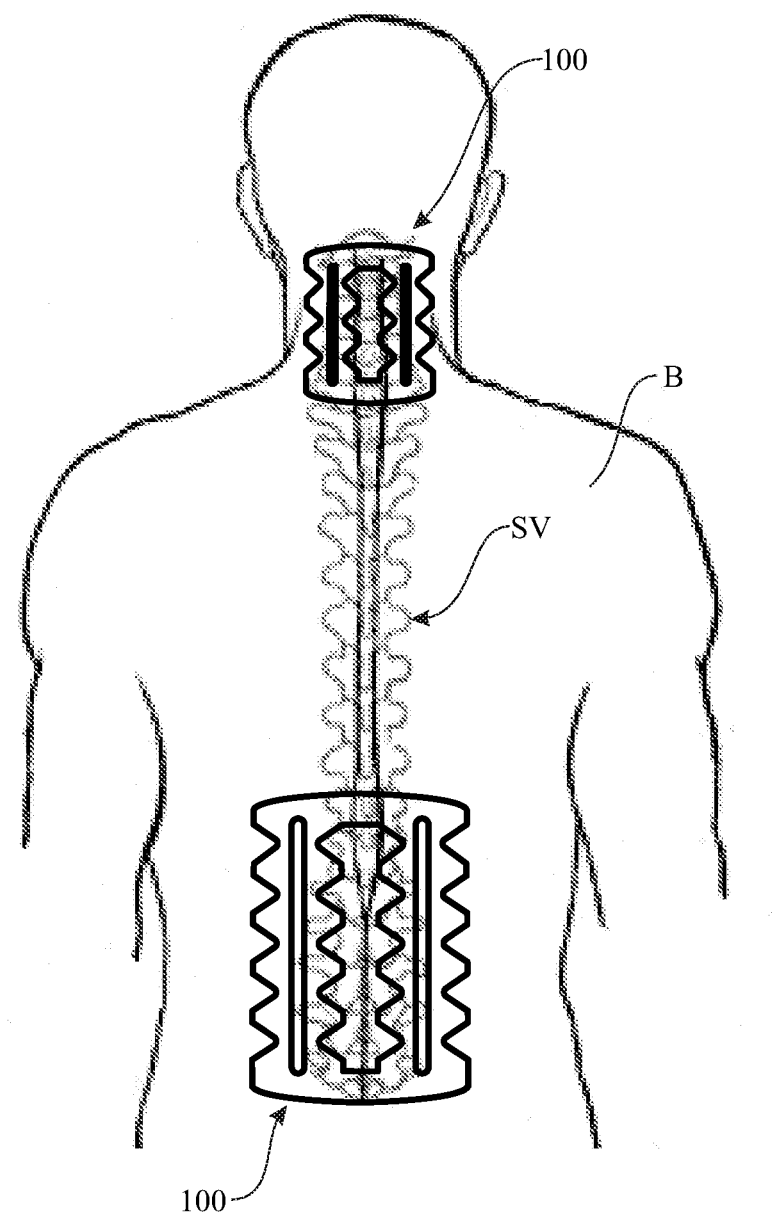
FIG. 6 presents the rear pictorial view of FIG. 5, depicting a pair of appropriately-sized spine support devices 100 affixed to the corresponding neck and lower back of the aforementioned person's body, shown properly positioned over the respective cervical and lumbar regions of the person's spine.

The stabilizing stirrups 110 protruding from the rear face 106 of the support plate 102 are in spaced-apart parallel relationship to one another and each is in a spaced relationship from respective ones of the opposite peripheral side edge portions 116, 118 and the opposing inner side edge portions 120, 122 of the support plate so as to augment the support provided by the support plate when the latter is positioned in contact with the portion of the person's back (see FIGS. 5 and 6). As best seen in FIG. 4, each of the stabilizing stirrups 110 includes an elongated outer body 128 defining an elongated cavity 130, and an elongated inner body 132 disposed in the elongated cavity. Further, each of the elongated outer and inner bodies 128, 132 and the elongated cavity 130 has a length and a width and is substantially greater in length than in width. The stabilizing stirrups 110 may come in different strengths allowing for more or less support depending on the kind of application needed.

Figure 2:
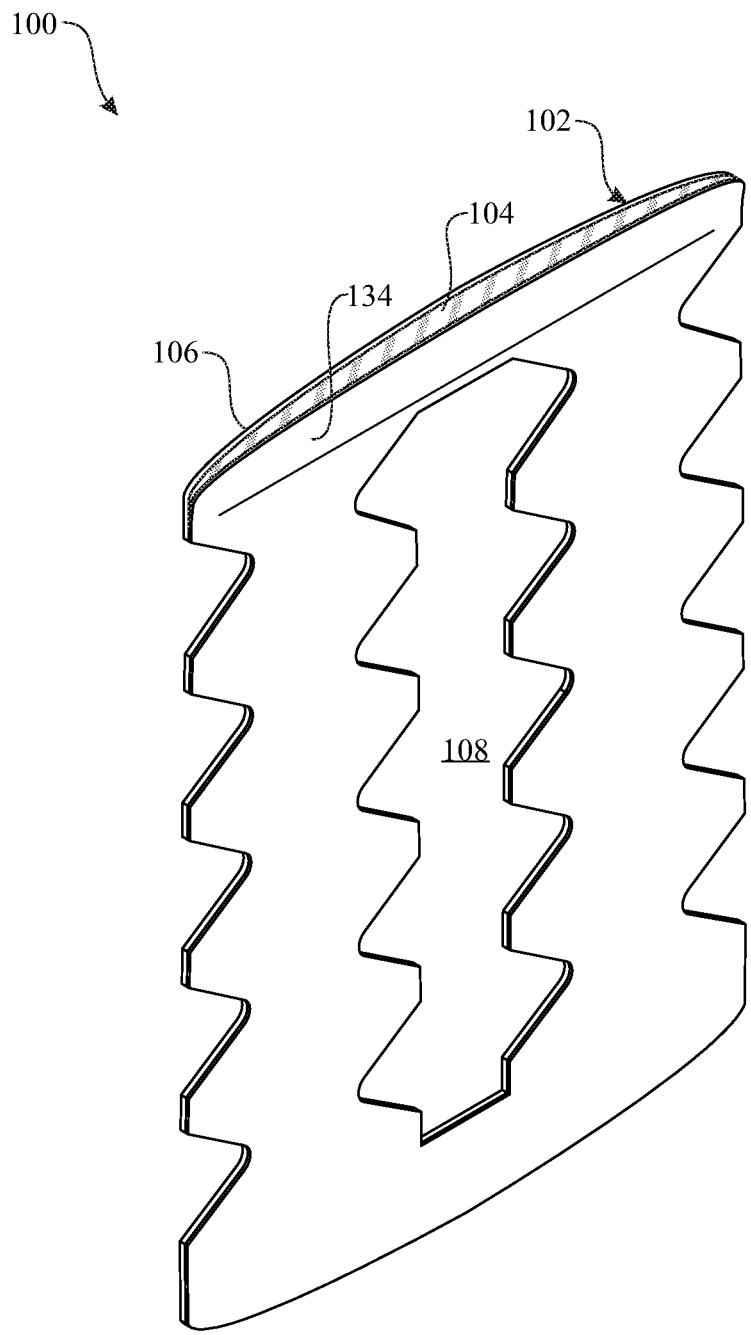
FIG. 2 presents a front isometric view of the spine support device originally introduced in FIG. 1.
Figure 3:
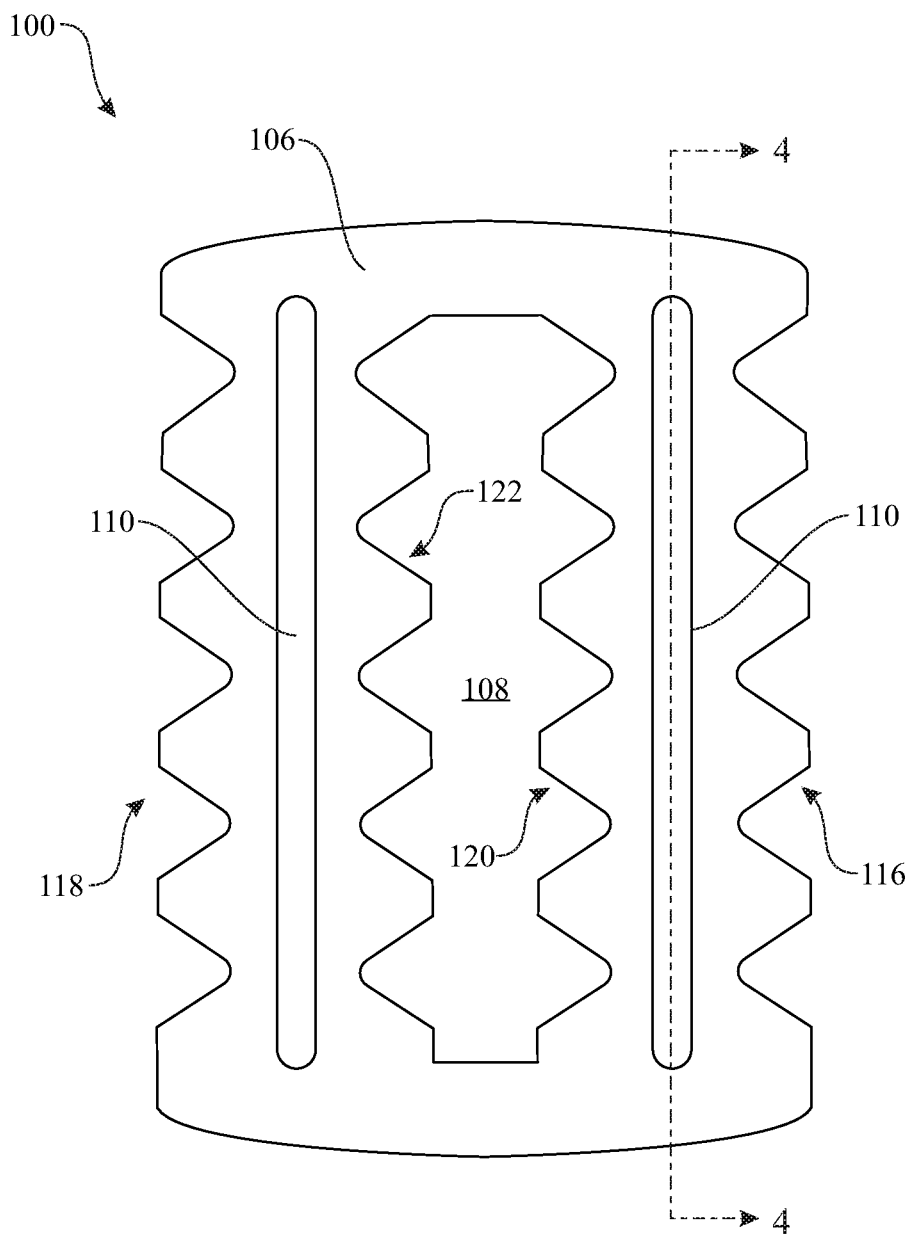
FIG. 3 presents a rear plan view of the spine support device originally introduced in FIG. 1.

FIGS. 5 and 6 illustrate where appropriately-sized models of the spine support device 100 may be applied to the person's back B so as to surround the cervical region C1-C7 and the lumbar region L1-L5 of the spinal vertebra SV of the person. Also, an appropriately-sized model of the spine support device 100 may be provided to surround a portion of the thoracic region of the spinal vertebra of the person. Further, the models may be appropriately-sized differently for youths than for adults. Still further, as shown in FIGS. 2 and 4, the support plate 102 may have a peelable sheet 134 covering an adhesive layer 136 on the front face 104. The adhesive layer 136 is provided for detachably attaching the support plate 102 to the portion of the person's back B surrounding the spinal vertebra region visible through the central opening 108 in the support plate.

FIGS. 7-9 and 10-12 respectively illustrate second and third exemplary embodiments of the spine support device, generally designated 200 and 300, which, in accordance with aspects of the present invention, basically include a support plate 202 and 302, having the same detailed make-up as the support plate 102 of the first exemplary embodiment described above. Thus, details of each support plate 202 and 302, being identified in FIGS. 7-9 and 10-12 by the same reference numerals except for the prefix "2", "3", may be reviewed with reference to detailed description of the support plate 102 and will not be repeated hereinafter. The respective second and third exemplary embodiments differ from the first exemplary embodiment and from one another with respect to their stabilizing stirrups having respective second and third designs.

Figure 7:
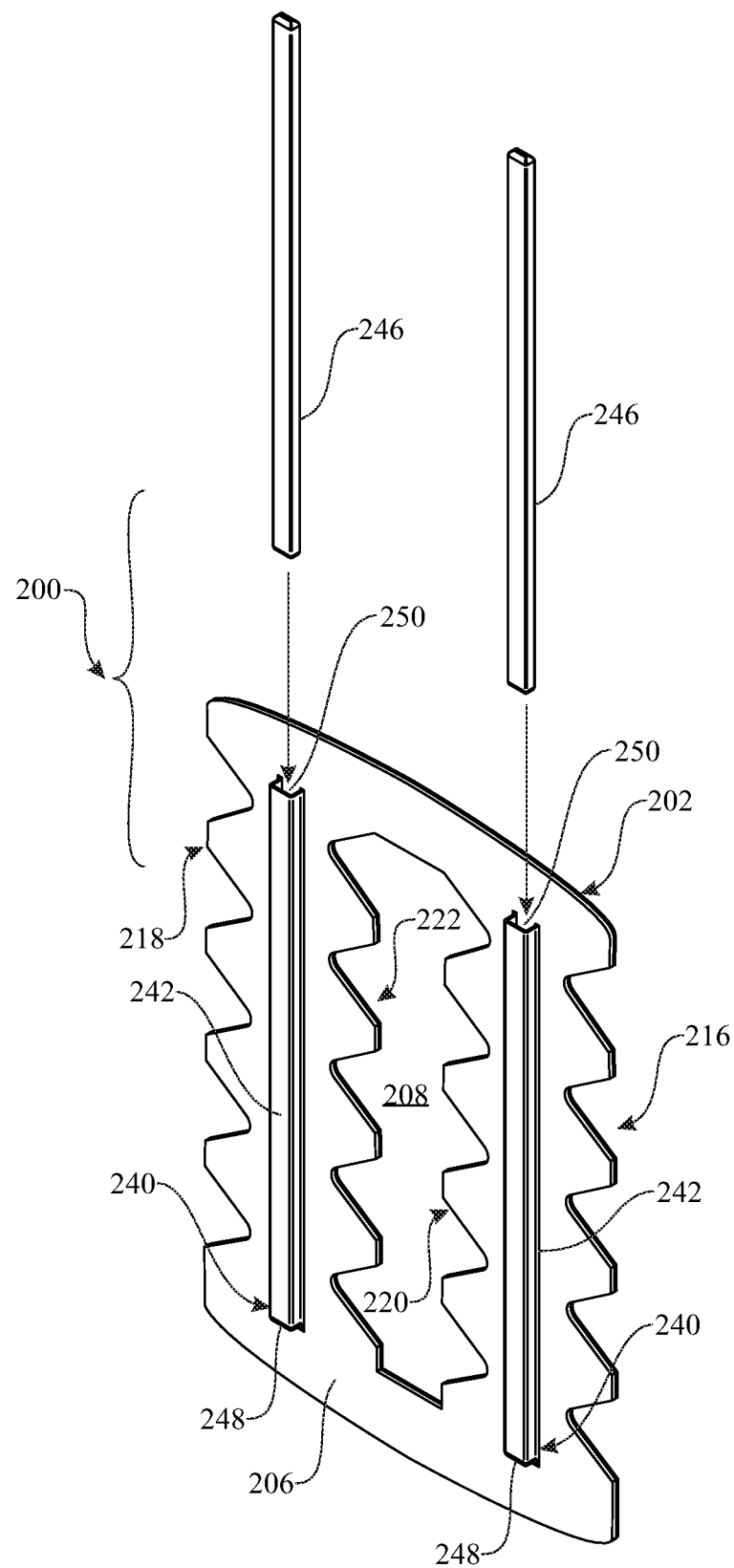
FIG. 7 presents a rear isometric view of a second exemplary embodiment of a spine support device, in accordance with aspects of the present invention, having a pair of stabilizing stirrups of a second design with portions thereof shown in exploded form.
Figure 8:
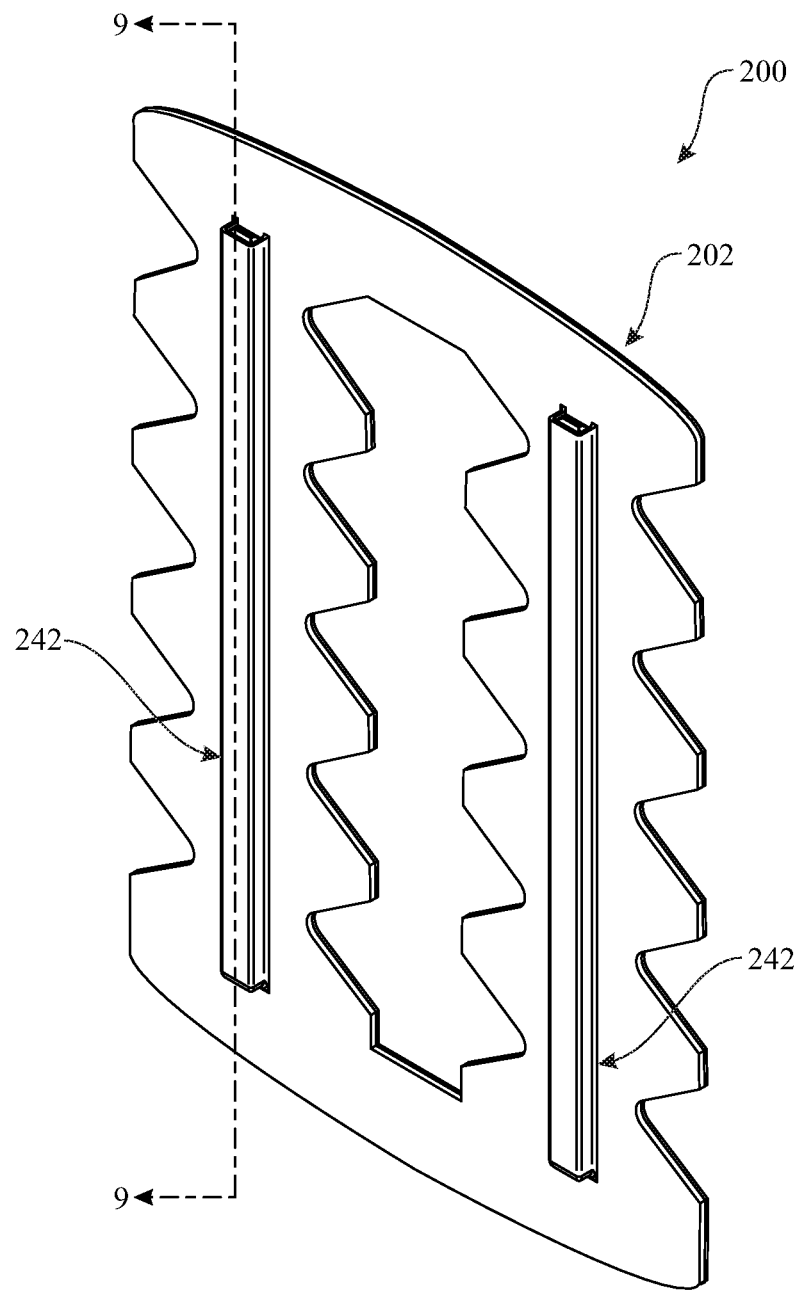
FIG. 8 presents an enlarged rear isometric view of the spine support device originally introduced in FIG. 7 having the pair of stabilizing stirrups of the second design with portions thereof shown in assembled form.
Figure 9:
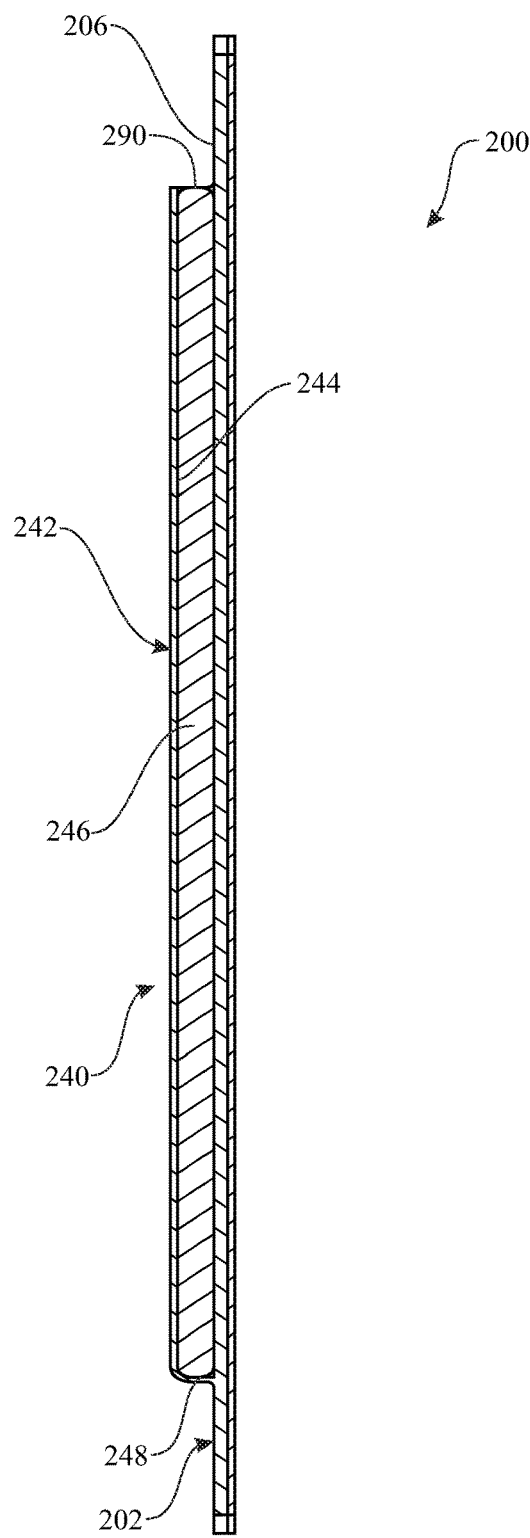
FIG. 9 presents an enlarged longitudinal sectional view of the spine support device as seen along line 9-9 of FIG. 8.

Referring now to FIGS. 7-9, there is illustrated the aforementioned second exemplary embodiment of the spine support device 200 having a pair of stabilizing stirrups 240 protruding from the rear face 206 of the support plate 202 in a spaced-apart parallel relationship to one another and each in a spaced relationship from respective ones of the opposite peripheral side edge portions 216, 218 and the opposing inner side edge portions 220, 222 of the support plate so as to augment the support provided by the support plate when the latter is positioned in contact with the portion of the person's back. Also, each of the stabilizing stirrups 240 includes an elongated outer body 242 defining an elongated cavity 244, and an elongated inner body 246 disposed in the elongated cavity. Further, each of the elongated outer and inner bodies 242, 246 and the elongated cavity 244 has a length and a width and is substantially greater in length than in width. As an alternative to the first exemplary embodiment, the elongated outer body 242 of each stabilizing stirrup 240 may have a closed lower end 248 and an open upper end 250. The elongated inner body 246 may be inserted through the open upper end 250 into the elongated cavity 244 of the elongated outer body 242 and rest upon the closed lower end 248 thereof. The support plate 202 may have access openings (not shown) along the elongated cavity 244 so that the elongated inner body 246 can be used to administer prescription medication to the back of the person.

Figure 10:
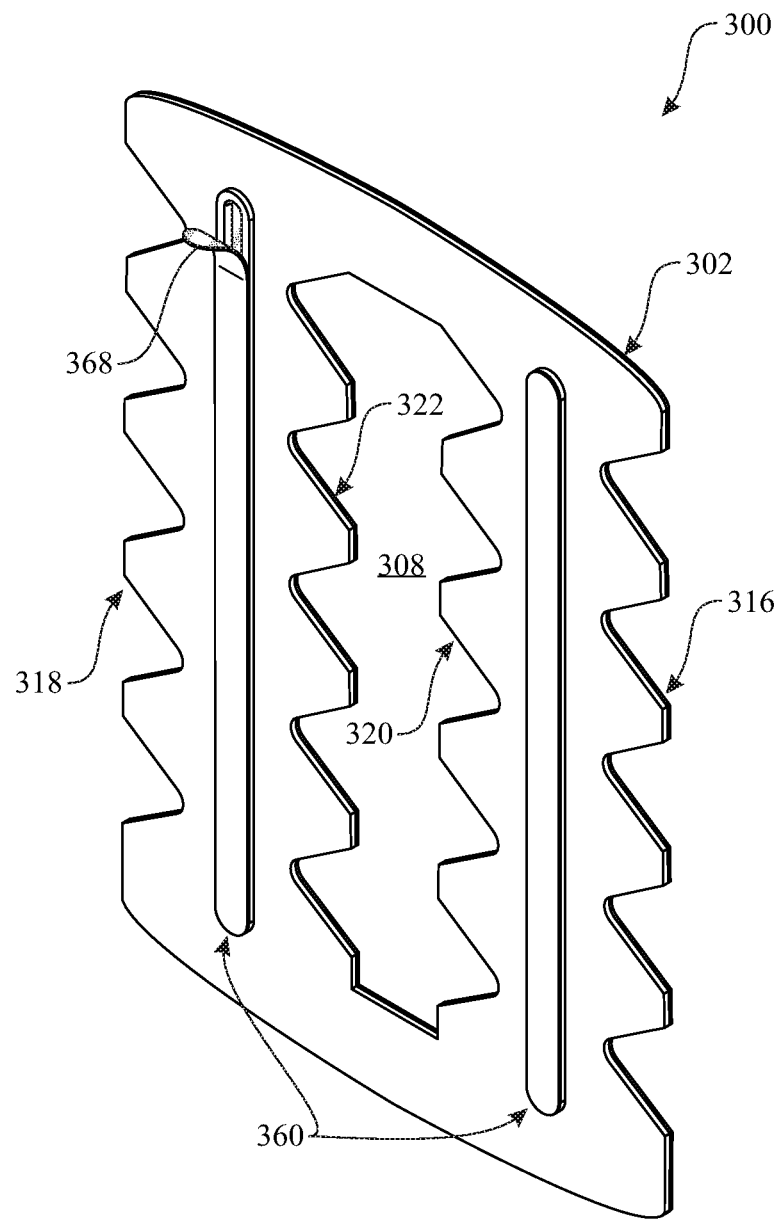
FIG. 10 presents a rear isometric view of a third exemplary embodiment of a spine support device, in accordance with aspects of the present invention, showing removal of a peelable strip covering an elongated cavity of each of a pair of stabilizing stirrups of a third design.
Figure 11:
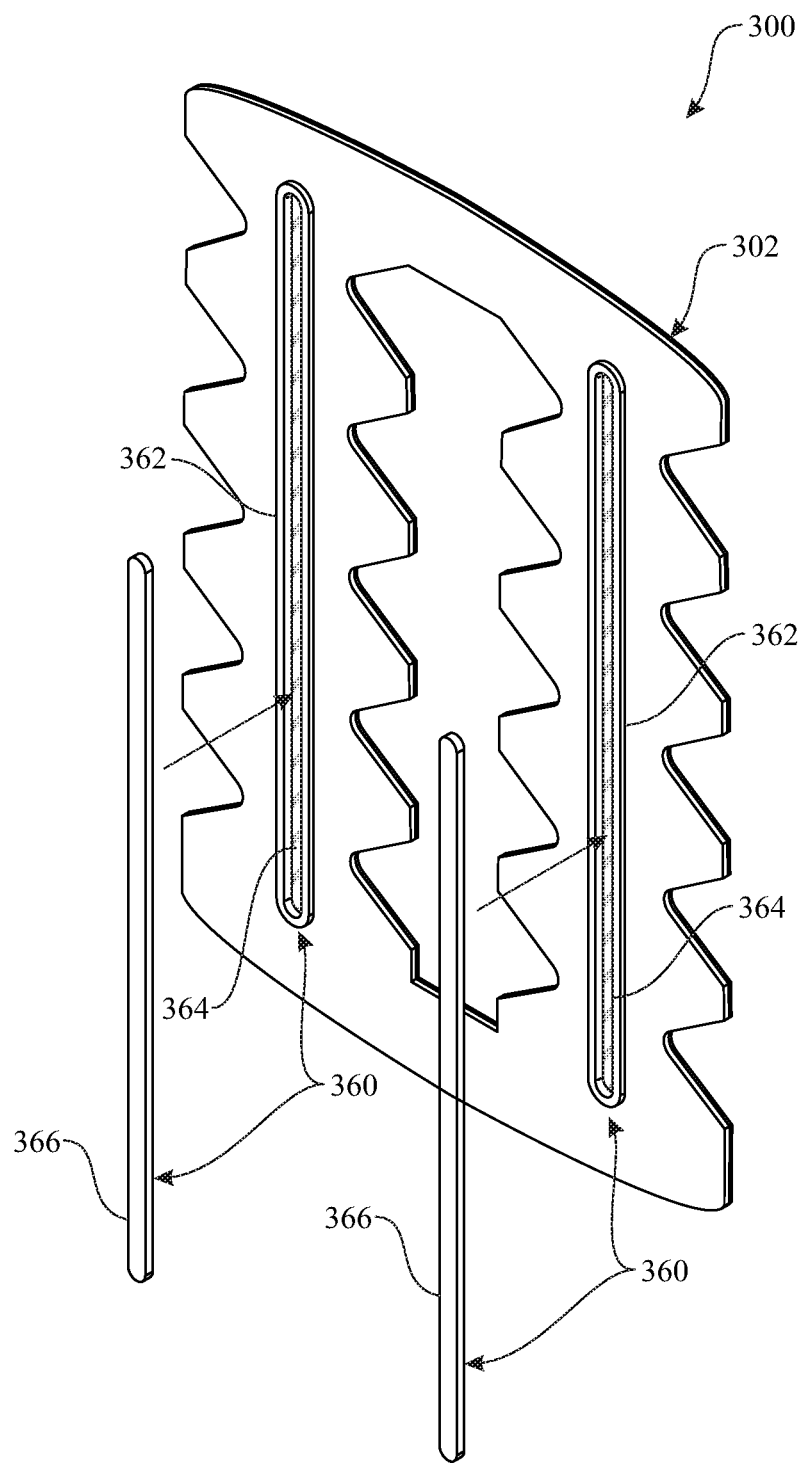
FIG. 11 presents a rear isometric view of the spine support device of FIG. 10 showing heated or cooled applicators aligned for insertion into cavities in the stabilizing stirrups of the third design.
Figure 12:
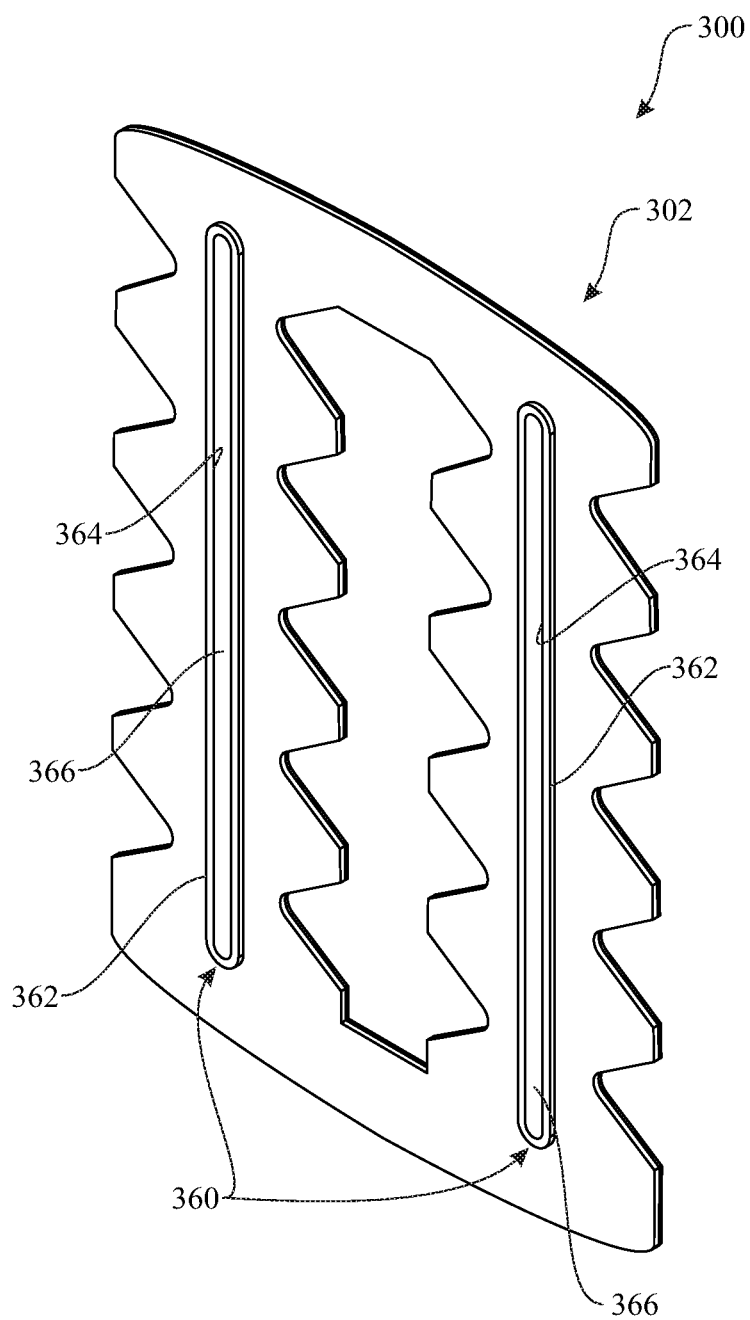
FIG. 12 presents a rear isometric view of the spine support device of FIG. 10 showing the applicators inserted into the stabilizing stirrups of the third design.

Referring now to FIGS. 10-12, there is illustrated the aforementioned third exemplary embodiment of the spine support device 300 having a pair of stabilizing stirrups 360 protruding from the rear face 306 of the support plate 302 in a spaced-apart parallel relationship to one another and each in a spaced relationship from respective ones of the opposite peripheral side edge portions 316, 318 and the opposing inner side edge portions 320, 322 of the support plate so as to augment the support provided by the support plate when the latter is positioned in contact with the portion of the person's back. Also, each of the stabilizing stirrups 360 includes an elongated outer body 362 defining an elongated cavity 364, and an elongated inner body 366 disposed in the elongated cavity. Further, each of the elongated outer and inner bodies 362, 366 and the elongated cavity 364 has a length and a width and is substantially greater in length than in width. As an alternative to the first and second exemplary embodiments, FIG. 10 shows the elongated outer body 362 of each stabilizing stirrup 360 having a strip 368 covering the elongated cavity 364. The strip 368 is being peelable therefrom to open the elongated cavity 364 and permit insertion of the elongated inner body 366, such as in the form of one of a heated applicator, a cooled applicator or a medicated applicator, into the opened elongated cavity 364.

Figure 13:
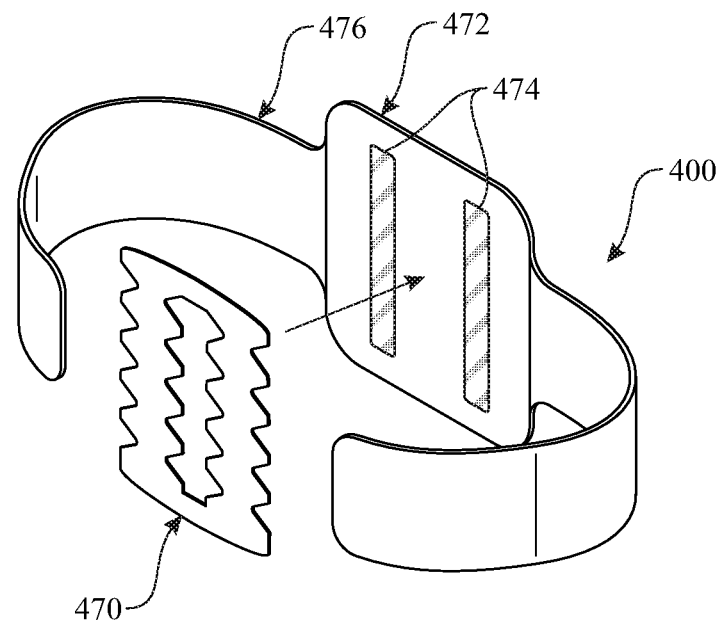
FIG. 13 presents a rear isometric view of a fourth exemplary embodiment of a spine support device, in accordance with aspects of the present invention, showing in exploded form the device having two portions with one of the portions being part of a belt for supporting the device on a person adjacent to the spine of the person.
Figure 14:
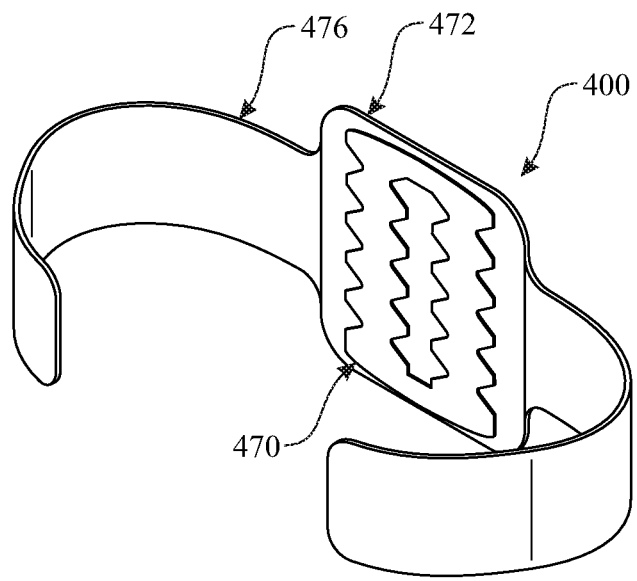
FIG. 14 presents a rear isometric view of the spine support device of FIG. 13 now showing the device in assembled form for supporting the device on the person.

Referring to FIGS. 13 and 14, there is illustrated a fourth exemplary embodiment of a spine support device, generally designated 400, which, in accordance with aspect of the present invention, is somewhat similar to the spine support device 100 of FIG. 1. Alternatively, however, the spine support device 400 basically includes two portions 470, 472. The one portion 470 has the make-up of the support plate 102 of the first embodiment without the stabilizing stirrups, whereas the other portion 472 with the stabilizing stirrups 474 is part of a belt 476 for supporting the spine support device 400 on the back of a person adjacent to the selected region of the spine of the person.

Figure 15:
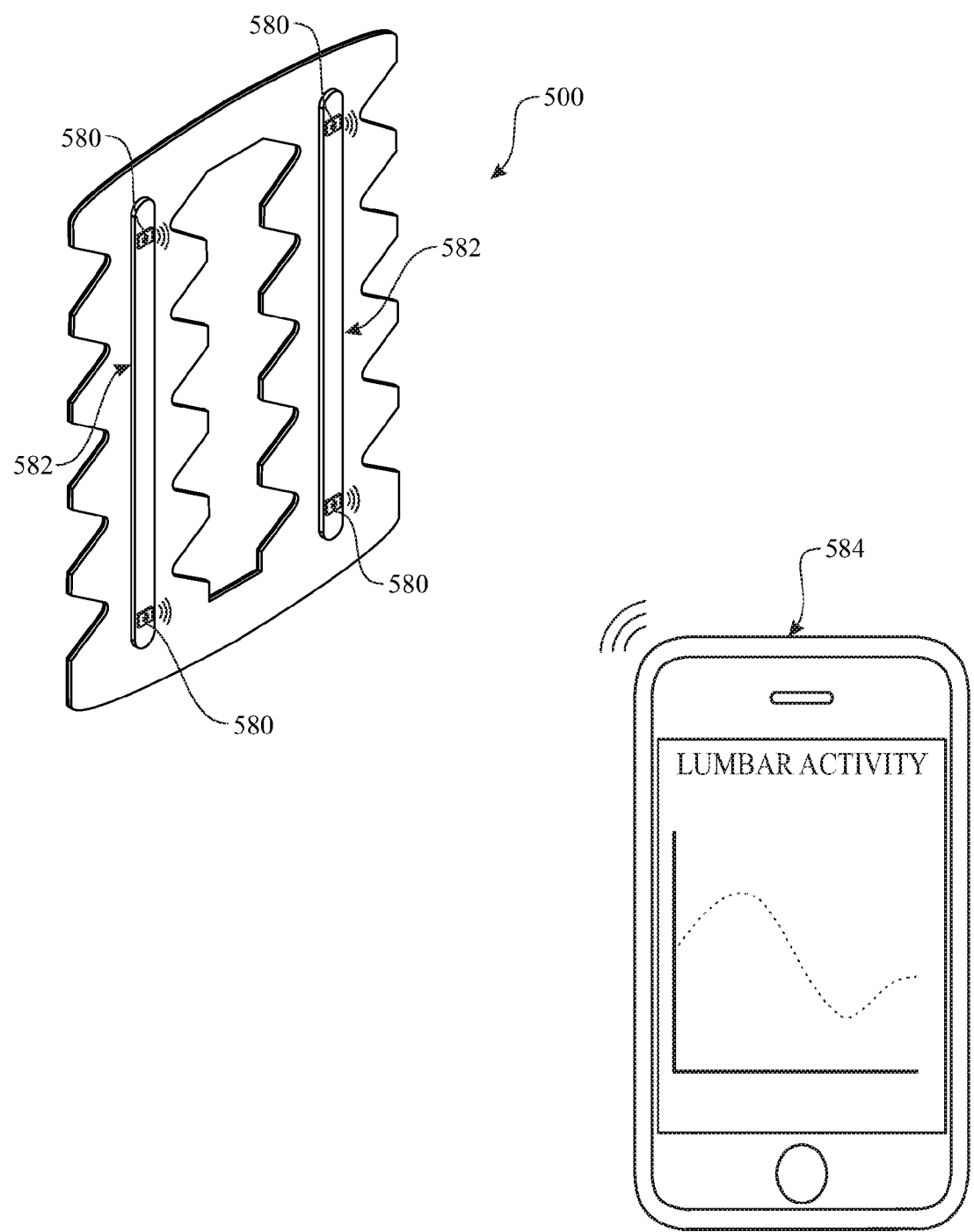
FIG. 15 presents a rear isometric view of a fifth exemplary embodiment of a spine support device, in accordance with aspects of the present invention, being similar to the device of FIG. 1 now showing vibratory actuators attached at opposite end portions of the stabilizing stirrups and an electronic device operable to activate the vibratory actuators and display activity of the portion of the spine supported by the device.

Referring last to FIG. 15, there is illustrated a fifth exemplary embodiment of a spine support device, generally designated 500, which, in accordance with aspects of the present invention, is similar to the spine support device 100 of FIG. 1. In this embodiment, the spine support device 500 has vibratory actuators 580 attached at opposite end portions of the stabilizing stirrups 582 and an electronic device 584 being operable to activate the vibratory actuators and display activity of the portion of the spine supported by the spine support device. Also, by using Bluetooth or any other appropriate technology to communicate data (continuous, periodic, etc.), the stabilizing stirrups 582 may be employed to sense different movements of the spine and keep a database of recorded information pertaining thereto.

To recapitulate, the several exemplary embodiments of the spine support device, as described above, incorporate design features that accommodate the natural anatomy of the spine. The support plate of the spine support device incorporates shapes that allow for natural bending and rotational movement that is generated by the spine to occur, facilitating more degrees of freedom which, in turn, allow the spine to move in a manner that is anatomically correct. Stabilizing stirrups are provided on the support plate that have a sufficient degree of stiffness or firmness to provide the spine with stability which is needed to proper alignment and support. The support plate and stabilizing stirrups may be manufactured by using conventional fabrication techniques and from suitable materials, such as conventional plastic.

Furthermore, there are multiple potential applications for the spine support device. It can be used in the medical/healthcare field to treat and reduce back pain. It can be utilized in the workplace to promote good health and reduce work stoppages. It can also be utilized in all types of athletic/recreational activities ranging from the novice person who just wants to walk to the various activities and endeavors of professional and Olympic athletes. The field of golf is one perfect fit for the device. However, its applications encompass all areas of sports including but not limited to tennis, biking and running.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A spine support device, comprising:
   a pliable support plate partially defined by a contiguous peripheral edge adjoining oppositely-facing front and rear faces, and a central opening extending in a longitudinal direction completely through the support plate and having an area defined by a contiguous support plate inner edge, the central opening particularly sized and shaped to define a central opening area for visibly exposing a desired area of a posterior surface of a user's body overlying a corresponding predetermined spine segment of a device user's spine when the spine support device is affixed to said posterior surface during use, wherein the spine segment includes a contiguous series of individual spinal vertebra and interconnecting facets of said contiguous series of individual spinal vertebra;

an adhesive layer disposed upon the support plate front face;

a removable protective sheet disposed over the adhesive layer such that the adhesive layer is interposed between the front face of the support plate and an interior surface of the removable protective sheet prior to affixing the spine support device to the posterior surface of the user's body during use of the device; and a pair of longitudinally-oriented stabilizing stirrups integrated with said rear face of said support plate in a spaced-apart parallel relationship to one another, each of said pair of longitudinally-oriented stabilizing stirrups incorporating a structure and composition chosen to define a stabilizing stirrup rigidity adequate to impart a predefined desired degree of support augmenting support provided by said support plate following adhesion of the front face of said support plate to said posterior surface of at least one of a back and neck region of the device user's body, the stabilizing stirrups further enabling and facilitating freedom of movement of the corresponding spine segment that remains exposed through the support plate central opening after the spine support device is affixed to the posterior surface of the user.

2. The device as recited in claim 1 wherein said support plate contiguous peripheral edge further comprises a pair of longitudinally-oriented, spaced-apart, opposite peripheral side edge portions, each of which is in the form of alternating peaks and valleys defining a corresponding series of peripheral side edge portion notches, wherein said longitudinally-oriented, spaced-apart opposite peripheral side edge portions are mirror images of one another to thereby enable and facilitate accommodation of the interconnecting facets of said contiguous series of individual spinal vertebra visible through said central opening of said support plate.

3. The device as recited in claim 2 wherein said longitudinally-oriented support plate central opening is partially defined by a pair of opposing, spaced-apart, longitudinally-extending inner side edge portions, each of said opposing inner side edge portions of said support plate central opening in the form of alternating peaks and valleys defining a series of inner side edge portion notches, wherein said opposing inner side edge portions are mirror images of one another to enable and facilitate accommodation of the interconnecting facets of the contiguous series of individual spinal vertebra visible through said central opening of said support plate.

4. The device as recited in claim 3 wherein said contiguous peripheral edge of said support plate further comprises a pair of spaced-apart opposite peripheral top and bottom edge portions having oppositely curved shapes that are mirror images of one another, the curved shapes of said top and bottom edge portions conforming to natural anatomy of the underlying spine and posterior surface of the user following adhesion of the front face of the support plate to the posterior surface of at least one of a back region and a neck region of the device user, to enable and facilitate rotation of the spine, and to enhance stability and support of the spine, wherein, when the device is used for supporting a lumbar spinal segment, said peripheral top edge portion of the support plate is shaped to conform to an anatomical shape and anatomical angles of distal aspects of a user's ribs, and the peripheral bottom edge portion of the support plate is shaped to conform to an anatomical shape and anatomical angles of a user's pelvic/sacral region, and wherein, when the device is used for supporting a cervical spinal segment, said peripheral top edge portion of the support plate is shaped to conform to an anatomical shape and anatomical angles of a user's occiput, and the peripheral bottom edge portion of the support plate is shaped to conform to an anatomical shape and anatomical angles of a user's proximal ribs.

5. The device as recited in claim 4 wherein the series of side edge notches along the peripheral side edge portions of said contiguous peripheral edge of said support plate are in lateral alignment with the corresponding series of notches of said opposing inner side edge portions of said support plate opening.

6. The device as recited in claim 3 wherein said support plate central opening is partially defined by top and bottom ends, said support plate top and bottom ends in the form of a pair of respective spaced-apart opposing upper and lower inner edge portions.

7. The device as recited in claim 1 wherein each of said pair of longitudinally-oriented stabilizing stirrups protrudes outwardly from said rear face of said support plate.

8. The device as recited in claim 1 wherein each of said pair of spaced-apart, longitudinally-oriented stabilizing stirrups further comprises:

an elongated outer body having an interior surface defining an elongated interior cavity; and an elongated inner body disposed within said elongated interior cavity, wherein, said elongated interior cavity defined by said interior surface thereof defines an interior cavity volume shaped to conform to a corresponding exterior surface of said elongated inner body, and sized nominally larger than said elongated inner body such that said elongated inner body substantially fills the interior cavity volume.

9. The device as recited in claim 8, wherein said elongated inner body is completely enclosed within said elongated outer body.

10. The device as recited in claim 9, wherein said elongated outer body further comprises an integral portion of said support plate in the form of an elongated enclosed pocket, said integral outer body portion further comprising a raised feature of said support plate protruding outwardly from the planar face thereof.

11. A spine support device, comprising:
a resilient support plate, comprising
front and rear opposite faces separated by an exterior perimeter including an exterior upper edge and an opposite exterior lower edge, each of said opposite exterior upper and lower edges having a curvature enabling said resilient support plate to conform to a posterior area of an individual during use of said spine support device, and
a central opening extending completely through said front and rear faces of said resilient support plate, said central opening having a shape defined by a contiguous interior edge, the contiguous interior edge including opposing upper and lower interior side edge portions, and opposing interior left and right lateral side edge portions, each of said opposing interior left and right lateral side edge portions having a zigzag line shape defining alternating peaks and valleys, said opposing interior left and right lateral side edge portions being in mirror image alignment to one another such that peaks of said left lateral side edge portion are in horizontal alignment with corresponding peaks of said right lateral side edge portion, and valleys of said left lateral side edge portion are in horizontal alignment with corresponding valleys of said right lateral side edge portion, said central opening accommodating interconnecting facets of a region of spinal vertebra of said individual visible through said central opening in said support plate when said support plate front face is positioned in contact with said posterior area of the individual during use of said spine support device; and a pair of stabilizing stirrups integrated with, and protruding outwardly from, said rear face of said support plate in spaced-apart parallel relationship to one another, and spaced a distance outwardly from said opposing interior lateral side edge portions of said support plate so as to augment support provided by said support plate when said support plate is positioned in contact with said posterior area during use, each of said stabilizing stirrups further comprising an elongated outer body defining an elongated cavity, and an elongated inner body disposed in said elongated cavity, said elongated outer and inner bodies both extending vertically in parallel alignment with one another.

12. A spine support device, comprising:
a support plate comprising
  front and rear faces,
  a central opening between said front and rear faces,
  opposite peripheral top and bottom edge portions spaced apart from one another, and
  opposite peripheral side edge portions spaced apart from one another and extending longitudinally between and interconnecting said opposite peripheral top and bottom edge portions, each of said opposite peripheral side edge portions having an alternating peak and valley shape such that said opposite peripheral side edge portions are mirror images of one another for accommodating interconnecting facets of a contiguous length of spinal vertebrae of a person visible through said central opening in said support plate when said support plate at said front face is positioned in contact with the person's back surrounding the spinal vertebra region that is intended to be supported by said support plate; and a pair of stabilizing stirrups integrated into, and protruding outwardly from, said rear face of said support plate in spaced-apart parallel relationship to one another, and spaced inwardly from said opposite peripheral side edge portions of said support plate so as to augment the support provided by said support plate when said support plate is positioned in contact with the portion of the person's back.

13. The device as recited in claim 12 wherein each of said opposite peripheral top and bottom edge portions have oppositely curved shapes being mirror images of one another.

14. The device as recited in claim 12 wherein:
said central opening of said support plate has opposing sides;
said support plate also has opposing inner side edge portions at said opposing sides of said central opening, each of said opposing inner side edge portions having an alternating peak and valley shape such that said opposing inner side edge portions are mirror images of one another for accommodating the interconnecting facets of the spinal vertebra region visible through said central opening in said support plate; and
said pair of stabilizing stirrups are disposed on said rear face of said support plate in a spaced relationship from said opposite peripheral side edge portions and said opposing inner side edge portions of said support plate.

15. The device as recited in claim 12 wherein each of said stabilizing stirrups comprises:
an elongated outer body defining an elongated cavity; and
an elongated inner body disposed in said elongated cavity.

* * * * *